United States Patent [19]
Taylor et al.

[11] 3,989,691
[45] Nov. 2, 1976

[54] PREPARATION OF CINCHONA ALKALOID INTERMEDIATES

[75] Inventors: Edward C. Taylor, Princeton, N.J.; Stephen F. Martin, Austin, Tex.

[73] Assignee: Princeton University, Princeton, N.J.

[22] Filed: Jan. 9, 1975

[21] Appl. No.: 539,669

Related U.S. Application Data

[63] Continuation-in-part of Ser. No. 321,428, Jan. 5, 1973, abandoned.

[52] U.S. Cl. .......................... 260/240 R; 260/283 S; 260/283 P; 260/287 CE; 260/295 R
[51] Int. Cl.$^2$ ....................................... C07D 401/06
[58] Field of Search ............... 260/287 CF, 287 CE, 260/287 R, 283 S, 240 R

[56] References Cited
UNITED STATES PATENTS 3,772,302  11/1973  Gutzwiller et al. ................. 260/284

OTHER PUBLICATIONS

Gates, "JACS" 92 pp. 205-207, (1970).

*Primary Examiner*—Nicholas S. Rizzo
*Assistant Examiner*—David E. Wheeler
*Attorney, Agent, or Firm*—James L. Rowe; Everet F. Smith

[57] ABSTRACT

4-[3-(3-vinyl-1-acetyl-4-piperidyl)-1-propenyl]-6-methoxyquinoline, the corresponding epoxide and related compounds, useful in the synthesis of Cinchona alkaloids, are prepared by introducing an ylid group in the 4-position of a suitably substituted quinoline and reacting this ylid with an N-acetyl-4-piperidineacetaldehyde.

8 Claims, No Drawings

PREPARATION OF CINCHONA ALKALOID INTERMEDIATES

CROSS REFERENCE

This application is a continuation-in-part of our copending application Ser. No. 321,428 filed Jan. 5, 1973 now abandoned.

BACKGROUND OF THE INVENTION

The first synthesis of a *Cinchona* alkaloid or of a compound having the ring structure of a *Cinchona* alkaloid was that of Rabe and co-workers who synthesized the compound dihydroquinine. [See Ber., 64, 2487 (1931)]. The first total synthesis of a naturally occurring *Cinchona* alkaloid, quinine, was carried out by R. B. Woodward and W. von E. Doering, *J. Am. Chem. Soc.*, 66, 849 (1944); id, 67, 860 (1945). This synthesis involved the reaction of dl-N-benzoyl-homomeroquinene ethyl ester with ethyl quininate in the presence of sodium ethoxide. This condensation yielded dl-quinotoxine which, after cyclization, was smoothly reduced with sodium isopropoxide to yield a mixture of quinine and quinidine. Pure quinine was produced after resolution of the racemic mixture into its optical antipodes. More recently, two groups of workers have developed syntheses of quinine and related *Cinchona* alkaloids which are more adaptable to large scale production than the classical Woodward-Doering synthesis. Uskokovic and co-workers in *J. Am. Chem. Soc.*, 92, 204 (1970) have reported a novel synthesis of quinine and quinidine involving the condensation of 6-methoxy lepidyl lithium with N-benzoyl-meroquinene methyl ester to yield a compound of the following structure (I).

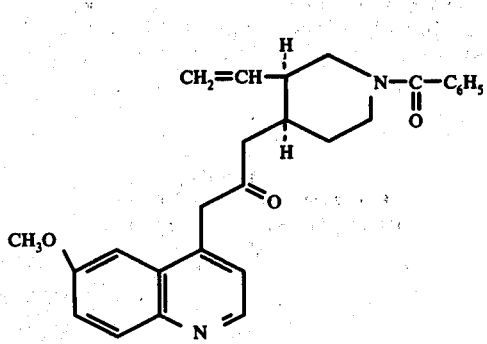

I

In a first route, reduction of this intermediate ketone with di-isobutylaluminumhydride yields a racemic alcohol which can be resolved by the use of dibenzoyl-(+)-tartaric acid to yield a compound of the following structure (II) wherein R'' is methoxy and R''' is vinyl.

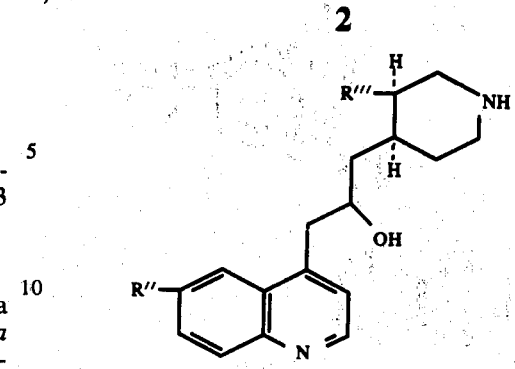

II

Treatment of this intermediate alcohol with dilute acid eliminates the elements of water from the quinoline side chain to yield an intermediate propene (III) wherein R'' and R''' have the same meaning as above.

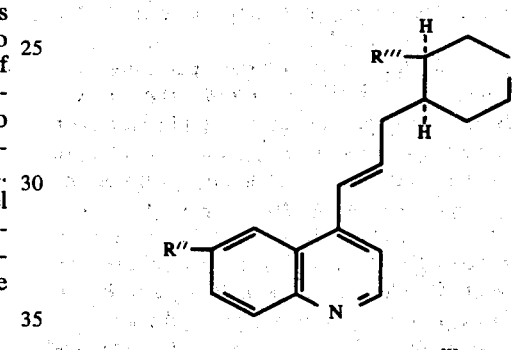

III

This propene spontaneously cyclizes to yield a mixture of desoxyquinine and desoxyquinidine (IV) wherein R'' and R''' have the previous significance.

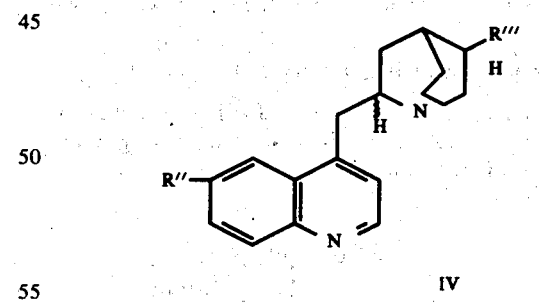

IV

Base catalyzed oxidation of the desoxyquinine-desoxyquinidine mixture yields, after separation by chromatography, quinine, quinidine, and a mixture of epiquinine and epiquinidine.

In a second route, the ketone (I wherein R'' is methoxy and R''' is vinyl) is brominated on the methylene alpha to the quinoline ring. Reduction of the ketone group with sodium borohydride yields an intermediate bromohydrin which is readily converted to the epoxide (V) wherein R'' and R''' have the same significance as before.

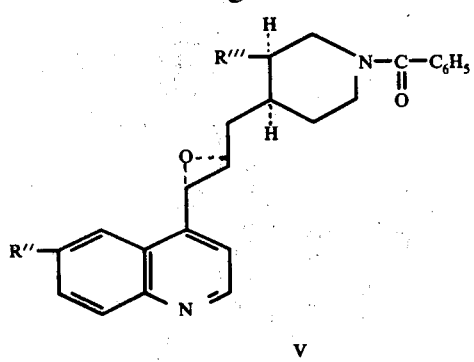

V

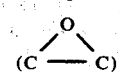

by reacting a quinoline of the formula:

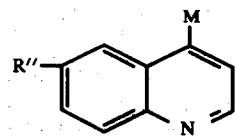

VII wherein R'' is H or methoxy and M is a group labile to nucleophilic displacement, such as a halogen or an akyl or aryl sulfonyl, with two equivalents of a Wittig reagent—a methylene phosphorane of the structure $CH_2=P(R'''')_3$—or with one equivalent of a Wittig reagent and one equivalent of a strong base such as sodium hydride, or when R'' is H and M is the same as before with two equivalents of a sulfurane of the structure $CH_2=S(R'''')_2$ or with one equivalent of $CH_2=S(R'''')_2$ and one sodium hydride to form an ylid of the formula:

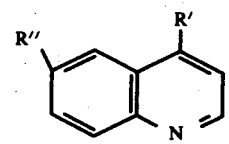

VIII wherein R'' is H or methoxy and R' is $CH=P(R'''')_3$ or R'' is H and R' is $CH=S(R'''')_2$ wherein each R'''' independently represents phenyl or $C_1$-$C_4$ alkyl such as n-butyl, n-propyl and the like groups. Treatment of the ylid with an N-acylpiperidine-acetaldehyde (IX)

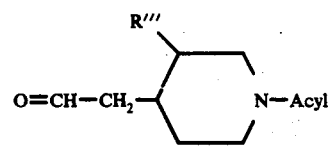

IX wherein R''' is H or vinyl, produces the desired intermediate (Structure VI above). Useful acyl groups include acetyl, benzoyl and the like.

Treatment of the epoxide with diisobutylaluminumhydride yields the unacylated piperidine which spontaneously cyclizes to yield the quinuclidine alcohol derivative (a mixture of quinine, quinidine and the corresponding epi compounds when R'' is methoxy and R''' is vinyl).

Uskokovic and co-workers also referred to the above synthetic procedure in an article appearing in *J. Am. Chem. Soc.*, 93, 5904 (1971).

Gates and co-workers in an article appearing in *J. Am. Chem. Soc.*, 92, 205 (1970) describe the condensation of N-acetyl-4-piperidineacetic acid ester with 6-methoxy lepidine to yield a ketone corresponding to Formula I above except that the benzoyl group on the piperidine nitrogen is replaced by a acetyl group. Reduction of the ketone to an alcohol and dehydration of the alcohol yields the N-acetyl derivative of the propane of formula III wherein R'' is methoxy and R''' is vinyl. Hydrolysis of the acetyl group yields the intermediate (III) above which spontaneously cyclizes to give the desoxyquinine-desoxyquinidine mixture (IV). Gates et al. also applied the synthesis to compounds in which R'' is methoxy and R''' is hydrogen to yield racemic 6-methoxyruban.

It is an object of this invention to produce the intermediates (III) and (V) by procedures which are relatively simple to carry out and which give greater yields of these intermediates than has heretofor been possible.

DESCRIPTION OF THE INVENTION

In fulfillment of the above and other objects, this invention provides a method of synthesizing compounds of the formula

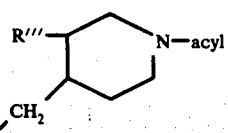

VI wherein R'' is H or methoxy, R''' is H or vinyl and Z is vinyl or 1,2-epoxy

In carrying out the above reaction sequence, an alkylidenephosphorane or an alkylidenesulfurane displaces, in a nucleophilic reaction, a suitable leaving group in the 4-position of the quinoline ring to yield an phosphorus ylid or a sulfur ylid. Suitable leaving groups include halo — particularly chloro, iodo and bromo —, $C_1$-$C_4$ alkylsulfonyl, $C_1$-$C_4$ alkylsulfonyloxy (mesyloxy for example) or $C_1$-$C_4$ alkylmercapto wherein the alkyl group can be methyl, ethyl, n-propyl, sec-butyl, isobutyl and the like; and arylsulfonyl, arylmercapto or arylsulfonyloxy (tosyloxy for example) wherein the aryl group can be α or β-naphthyl, phenyl, o, m and p-trifluoromethylphenyl, o,m and p-chlorophenyl, o,m and p-iodophenyl, o,m and p-bromophenyl, o,m and p-fluorophenyl, o,m and p-tolyl, o,m and p-anisyl, o,m and p-phenetolyl (ethoxyphenyl), o,m and p-ethylphenyl, o,m and p-nitrophenyl, o,m and p-acetylphenyl, o,m and p-propionylphenyl and the like. At least two equivalents of the phosphorane or sulfurane are preferably employed in the nucleophilic displacement reaction. Strong bases for use in the reactions of this invention in place of a second mole of phosphorane or sulfurane include strong, nonnucleophilic bases such as sodium and potassium hydride and the like. Other strong bases such as butyl lithium, diazabicyclononane, diazabicycloundecane, potassium t-butoxide, lithium di-isopropylamide, sodium methylate and sodium amide can also be used; but, as will be recognized by those skilled in the art, reaction conditions using bases of these types must be designed to avoid excessive irreversible reaction of the base with 4-chloroquinoline or a substituted 4-chloroquinoline. A suitable inert solvent such as 1,2-dimethoxyethane is used as the reaction medium. Reaction of the phosphorus ylid with an N-acyl-4-piperidineacetaldehyde, or with its 3-vinyl derivative, yields a propene according to formula VI above wherein Z is CH=CH. Similarly, reaction of the sulfur ylid with an N-acyl-4-piperidineacetaldehyde (or its 3-vinyl derivative) yields an epoxide according to formula VI above wherein Z is 1,2-epoxy. Alkaline hydrolysis of the N-acyl group in compounds of formula VI when Z is vinyl yields a piperidine derivative which can spontaneously cyclize to a quinuclidine derivative (formula IV above and related stereoisomers). Base catalyzed oxidation of this quinuclidine derivative with molecular oxygen yields a mixture of compounds hydroxylated on the carbon alpha to the quinoline ring having the following structure (X)

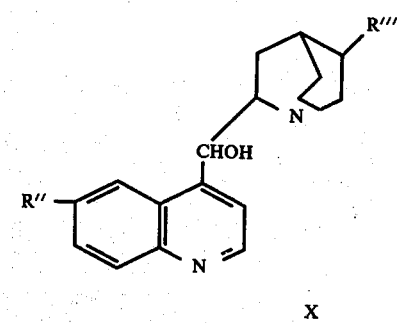

X wherein R" is H or methoxy and R''' is H or vinyl. The mixture can be separated into its components by chromatography. Basic or acidic hydrolysis of the N-acyl group in compounds of formula VI when Z is 1,2-epoxy directly yields the quinuclidine alcohol (X).

More specifically, this invention provides a method of synthesizing *Cinchona* alkaloid intermediates of the formula (XI):

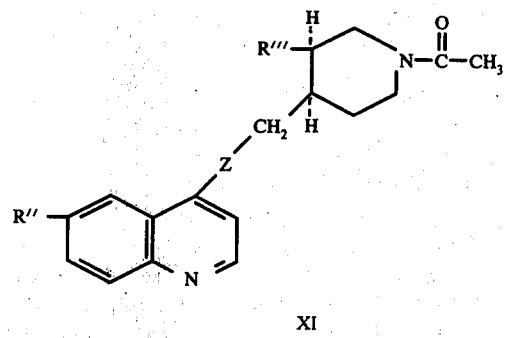

XI wherein R" is hydrogen or methoxy, R''' is hydrogen or vinyl, and Z is vinyl or 1,2-epoxy, by reacting a quinoline of the formula XII

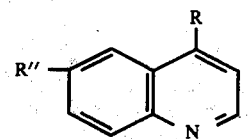

XII wherein R" is hydrogen or methoxy and R is Cl or $SO_2$—$CH_3$, with two equivalents of methylene triphenylphosphorane, or with one equivalent of methylene triphenylphosphorane and one equivalent of a strong base such as sodium hydride, when R is Cl and R" is H or methoxy or with two equivalents of methylene diphenylsulfurane or with one equivalent of methylene diphenylsulfurane and one equivalent of a strong base such as sodium hydride, when R" is H and R is $SO_2$— $CH_3$, to yield an ylid of the formula (XIII)

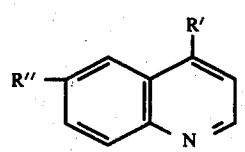

XIII wherein R' is CH= P(C₆H₅)₃ or CH=S(C₆H₅)₂ and R'' is H or methoxy, and then reacting said ylid when R' is CH = P (C₆H₅)₃ with a substituted piperidine of the formula (XIV)

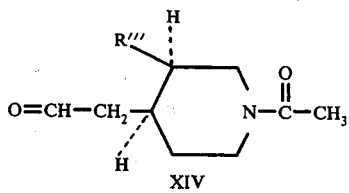

wherein R''' is H or vinyl to yield a compound according to formula XI above wherein Z is CH=CH or, when R' is CH=S(C₆H₅)₂ and R'' is H, to yield a compound of formula XI above wherein Z is 1,2-epoxy and R'' is H. Basic hydrolysis of the N-acetyl group either yields an intermediate piperidine which cyclizes to form a 4-quinuclidinylmethylquinoline such as desoxyquinine, desoxyquinidine, ruban or the like derivatives and which can be oxidized to racemic mixtures of *Cinchona* alkaloids or yields a piperidine which cyclizes directly to the quinuclidine alcohol itself, including mixtures of quinine and quinidine and their epi derivatives, cinchonine, cinchonidine, and their epi derivatives, mixtures of racemic erythro and racemic threorubanol etc. These mixtures can be separated into their components by chromatography.

The following Table 1 gives the names of the particular *Cinchona* alkaloid or related compound represented by formula XV below which can be prepared from the intermediates of this invention, depending upon the particular substituents for R'' and R''' and without reference to the stereochemistry involved.

TABLE I

| R'' | R''' | Cinchona alkaloid |
|---|---|---|
| H | H | rubanol |
| CH₃O | H | 6-methoxyrubanol |
| CH₃O | vinyl | quinine |
| | | quinidine |
| | | epi-quinine |
| | | epi-quinidine |
| H | vinyl | cinchonine |
| | | cinchonidine |
| | | epi-cinchonine |
| | | epi-cinchonidine |

With regard to the stereochemistry involved, *Cinchona* alkaloids commonly have 4 chiral carbon atoms at positions 3, 4, 8, and 9 as illustrated in formula XV below

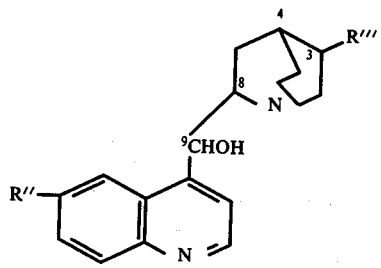

wherein R'' is H or methoxy and R''' is H or vinyl. In the related alkaloid, rubanol, wherein R'' and R''' are both hydrogen, or in 6-methoxy rubanol wherein R'' is methoxy and R''' is H, there are only three chiral centers, those 4, 8, and 9. All the naturally occurring *Cinchona* alkaloids have identical spatial configurations at carbon atoms 3 and 4. When a piperidineacetaldehyde derived from meroquinene (formula XIV above) is employed in the synthesis of the intermediates of this invention, the stereochemistry of the piperidine ring is set and the alkaloids and alkaloid intermediates produced by the reaction of a meroquinineacetaldehyde with the quinoline ylid yields compounds whose stereochemistry at carbons 3 and 4 is identical to that of the natural alkaloids. In formula XIV, the stereochemistry is specified by showing that the acetaldehyde group at 4 and the vinyl group at 3 are on the same side of the piperidine ring (shown by solid lines) and that the hydrogens (which become the hydrogens at the 3 and 4 position in formula XV above) are also both on the same side of the piperidine ring but opposite from the acetaldehyde and vinyl groups as shown by the dotted lines. The ring closure reaction of the propene intermediates of this invention (III), whereby a quinuclidine ring is formed, gives rise to C-9 desoxy compounds in which the configuration at C-8 is either "cis" (in which the —CH₂—CH₂— bridge is on the same side of the piperidine ring as the quinoline moiety), or "trans" (in which the —CH₂—CH₂— bridge is on the opposite side of the piperidine ring from the quinoline moiety); i.e., to products which are epimeric at C-8, corresponding to desoxyquinine and desoxyquinidine, or to desoxycinchonidine and desoxycinchonine, respectively. Oxidation of the methylene group at C-9 in IV then introduces a hydroxyl group preferentially in the erythro configuration (giving rise to the natural quinine-quinidine, cinchonidine-cinchonine, etc. series), as well as to a much smaller amount of the threo products (epiquinine-epiquinidine, epicinchonidine-epicinchonine). Ring closure of the trans epoxy intermediate gives rise to the erythro series of C-9 hydroxylated products (i.e., cinchonidine-cinchonine); the much smaller amount of cis epoxide formed in the sulfurane reaction gives rise to threo (epi) products.

In the examples that follow, the alkylidenephosphoranes and sulfuranes are exemplified as containing only phenyl groups. It will be apparent to those skilled in the art, however, that alkyl groups can replace phenyl groups in such reagents without any change in reactivity. For example, methylene tris-n-butylphosphorane is an eminently suitable Wittig reagent for use in the synthesis of this invention. Similarly, the sole inert solvent used for the reactions of the following Examples, which exemplify the processes of this invention, is 1,2-dimethoxyethane. However, other solvents such as tetrahydrofuran, diglyme [(bis(2-methoxyethyl)ether] and the like are also fully operative.

It is an advantage of the synthetic processes of this invention that, as will be seen from the following examples, all of the reactions can take place within a single vessel including the further steps of hydrolysis, cyclization, and oxidation or of hydrolysis and cyclization, depending upon the nature of the intermediate produced, to produce quinine or related compounds.

The following examples further exemplify the processes of this invention.

EXAMPLE 1

Preparation of N-acetyl-4-piperidineacetaldehyde

A 55 percent dispersion of sodium hydride in mineral oil containing 3.24 g. of a 55% dispersion of sodium hydride in mineral oil was washed with three 50 ml portions of dry pentane and then the sodium hydride was suspended in 100 ml of anhydrous 1,2-dimethoxyethane (to be referred to hereinafter as DME). 16.58 g. of triethylphosphonoacetate in 50 ml of anhydrous DME were added to the sodium hydride suspension under a nitrogen atmosphere slowly with stirring and cooling to about 0° C. After the addition had been completed, the ice bath was removed and the mixture stirred for an additional hour at ambient temperature. The ice bath was then replaced and a solution of 10 g. of N-benzoyl-4-piperidone in 25 ml of anhydrous DME was added in dropwise fashion with stirring. After this addition had been completed, the ice bath was again removed and stirring continued for about three hours. Excess solvents were removed in vacuo from the reaction mixture. About 100 ml of an ice-water mixture were added. The resulting aqueous mixture was extracted with three 100 ml portions of ether, and the ether extracts separated, combined and dried. Removal of the ether therefrom in vacuo yielded a residue comprising N-benzoyl-4-(carbethoxymethylene) piperidine formed in the above reaction. Recrystallization of the residue from hexane yielded about 11.7 g. of colorless prisms of N-benzoyl-4-(carbethoxymethylene) piperidine melting at about 102°–103° C. N-benzoyl-4-(carbethoxymethylene) piperidine thus prepared had the following physical characteristics. Boiling point = 178°–180° C. at 0.03 mm Hg.

nmr (CDCL$_3$): $\delta$1.28 (5, 3), 2.38 (broad m, 2), 3.05 (broad m, 2), 3.67 (broad m, 4), 4.18 (q, 2), 5.78 (broad s, 1), 7.41 (s, 5).

ir (KBr): 1715, 1660, 1620 cm$^{-1}$.

Anal: Calcd. for C$_{16}$H$_{19}$NO$_3$: C, 70.31; H, 7.01; N, 5.13. Found: C, 70.42; H, 7.10; N, 5.07.

16.4 g. of the above piperidine were dissolved in 300 ml of ethanol to which was added 1.0 g. of 10 percent Pd/C. The mixture was placed in a low pressure hydrogenation apparatus and hydrogenated at a pressure of about 60 psi. The catalyst was removed by filtration and the solvents evaporated from the hydrogenation mixture in vacuo. N-benzoyl-4-(carbethoxymethyl)-piperidine formed in the above reaction remained as a residue and was purified by distillation. A yield of about 15.86 g. of the compound was obtained distilling in the range 176°–178° C. at 0.20 mm Hg. The compound also crystallized from hexane in colorless prisms, mp=47°–48° C. The compound had the following physical characteristics.

nmr (CDCl$_3$): $\delta$ 1.23 (t, 3), 4.13 (q, 2; 2 also buried under the q), 1.2–3.2 (broad series of m, 9), 7.36 (s, 5).

ir (neat): 1735, 1630 cm$^{-1}$.

Anal: Calcd. for C$_{16}$H$_{21}$NO$_3$: C, 69.79; H, 7.69; N, 5.09. Found: C, 69.73; H, 7.63; N, 5.09.

A solution was prepared containing 5 g. of N-benzoyl-4-(carbethoxymethyl)piperidine in 50 ml of anhydrous toluene. The solution was cooled to about −75° C. under a dry nitrogen atmosphere. 38.3 ml of a 20 percent solution of di-isobutylaluminum hydride in hexane were added slowly with stirring. After the addition had been completed, the reaction mixture was stirred for an additional 3 hours; then 25 ml of 6 N aqueous hydrochloric acid were added. The aqueous layer was separated, washed with methylene chloride, the methylene chloride layer separated and discarded and the aqueous layer neutralized with solid sodium bicarbonate. The resulting amorphous solid was removed by suction filtration and discarded. The filtrate was concentrated in vacuo with gentle heating to a volume of about 50 ml. The resulting solution was saturated with solid sodium chloride and cooled to a temperature in the range 0° – 5° C. with an ice/salt bath. To this solution was added simultaneously with vigorous stirring a solution of 15 g sodium acetate in 15 ml of water and 15 ml of acetic anhydride. After the simultaneous additions had been completed, the reaction mixture was stirred for additional 30 minutes. Excess acid was neutralized with solid sodium carbonate and the resulting aqueous solution extracted with four 75 ml portions of methylene chloride. The methylene chloride extracts were combined and dried and the solvent removed therefrom by evaporation in vacuo. A yield of about 2.31 g of N-acetyl-4-piperidineacetaldehyde boiling in the range 88°–90° C. at 0.03 mm Hg was obtained. The compound had the following physical characteristics.

nmr (CDCl$_3$): $\delta$ 1.0–4.8 (broad series of m's, 11), 2.05 (s, 3), 9.81 (t, 1, J = 1.5 Hz).

ir (neat): 2735, 1725, 1635 cm$^{-1}$.

Anal: Calcd. for C$_9$H$_{15}$NO$_2$: C, 63.55; H, 9.27; N, 7.98. Found: C, 63.88; H, 8.94; N, 8.28.

EXAMPLE 2

Preparation of N-Acetyl-3(R)-vinyl-4(S)-piperidineacetaldehyde

Following the above procedure, N-benzoylmeroquinene methyl ester was reduced with di-isobutylaluminum hydride to yield N-acetyl-3(R)-vinyl-4(S)-piperidineacetaldehyde, which was isolated and purified by the above procedure. N-acetyl-3(R)-vinyl-4(S)-piperidineacetaldehyde thus produced distilled in the range of 110°–112° C. at 0.04 mm Hg. The compound had the following physical characteristics:

nmr (CDCl$_3$): $\delta$ 1.0–4.8 (series of broad m's, 10), 2.04 and 2.08 (2 d's, 3, J $\approx$ 1 Hz), 5.15 (m, 2), 5.80 (m, 1), 9.78 (perturbed t, 1, J $\approx$ 1.5 Hz). ir (neat): 2740, 1725, 1640, 1005, 920 cm$^{-1}$.

Exact mass calcd. for C$_{11}$H$_{17}$NO$_2$: 195.125921. Measured mass: 195.125313.

EXAMPLE 3

Preparation of Racemic Ruban

A suspension containing 6.34 g of methyltriphenylphosphonium bromide in 75 ml of anhydrous DME was cooled to a temperature in the range −30° to −35° C. under a dry nitrogen atmosphere. A solution of 7.1 ml of 2.5 N n-butyllithium in hexane was added, the resulting reaction mixture stirred for about one hour and then a solution of 1.70 g of 4-chloroquinoline in 10 ml of anhydrous DME was added. The reaction mixture was allowed to warm slowly to ambient temperature and was then heated to refluxing temperature for about 24 hours. The reaction mixture was then cooled to about −50° C. and a solution of 1 g of N-acetyl-4-piperidineacetaldehyde in 10 ml of anhydrous DME was added with stirring. After the addition had been completed, the cooling bath was removed and stirring continued at ambient temperature for about 24 hours. The precipitated phosphonium salts were separated by filtration, and the filtrate concentrated in vacuo. The resulting residue consisted of 4-[3-(1-acetyl-4-piperidyl)-1-propenyl]-quinoline formed in the above reaction.

Alkaline hydrolysis of 4-[3-(1-acetyl-4-piperidyl)-1-propenyl]quinoline yielded 4-[3-(4-piperidyl)-1-propenyl]-quinoline which spontaneously cyclized to yield racemic ruban. (The procedure of Gates et al., *J. Amer. Chem.*, 92, 205 (1970) was followed).

Following the procedure of Gutzwiller and Uskokovic, id, 204, oxidation of racemic ruban produced a mixture of racemic erythro and racemic threo-rubanol.

EXAMPLE 4

Preparation of Racemic 6-Methoxyruban.

Following the procedure of Example 3, 4-chloro-6-methoxyquinoline was reacted with the reaction product of methyl triphenylphosphonium bromide and n-butyllithium. This reaction product was then reacted with N-acetyl-4-piperidine-acetaldehyde to produce 4-[3-(1-acetyl-4-piperidyl)-1-propenyl]-6-methoxyquinoline.

Hydrolysis of the N-acetyl group yielded 4-[3-(4-piperidyl)-1-propenyl]-6-methoxyquinoline which cyclized spontaneously to form racemic 6-methoxyruban.

EXAMPLE 5

Preparation of Desoxyquinine and Desoxyquinidine

Following the procedure of Example 3, 4-chloro-6-methoxyquinoline was reacted with methylene triphenylphosphorane to yield the corresponding phosphorus ylid. Reaction of the ylid with N-acetyl-3(R)-vinyl-4(S)-piperidineacetaldehyde gave 4-[3-(3(R)-vinyl-1-acetyl-4(S)-piperidyl)-1-propenyl]-6-methoxy quinoline.

Removal of the N-acetyl group with base gave a piperidine derivative which spontaneously cyclized to yield a mixture of desoxyquinine and desoxyquinidine. Oxidation of the desoxyquinine-desoxyquinidine mixture by the procedure of Gutzwiller and Uskokovic (loc. cit.) yielded a mixture of quinine, quinidine, epiquinine and epiquinidine. These products were separated by preparative layer chromatography to yield purified quinine, purified quinidine, and a mixture of epiquinine and epiquinidine. These products were identical to those previously obtained by other workers.

EXAMPLE 6

Preparation of Racemic erythro and Racemic threo rubanol

A suspension of 4.25 g. of diphenyl methylsulfonium tetrafluoroborate [synthesized by the method of Hashimoto et al., *Nippon Kagaku Zasshi*, 87, 456 (1966)] was prepared in 60 ml of anhydrous DME under a dry nitrogen atmosphere. The suspension was cooled to −75° C. Next, a cold solution of lithium di-isopropylamide (prepared from di-isopropylamine and n-butyllithium) was added. The mixture was stirred for one hour after the addition had been completed at which point 1.84 g of 4-methylsulfonylquinoline, prepared by the method of Barlin and Brown, *J. Chem. Soc.* (B), 736 (1967), in 15 ml of warm anhydrous DME was added slowly. The reaction mixture was allowed to warm slowly to a temperature in the range −30° to −35° C. and stirring was continued for additional five hours at that temperature. The reaction mixture was then cooled to about −50° C. and N-acetyl-4-piperidineacetaldehyde was added as a solution of 1 g. of aldehyde in 5 ml of anhydrous DME. The reaction mixture was maintained at −30° to −35° C. for one hour and was then stirred over night at ambient temperature. The solvent was removed by evaporation in vacuo and the residue partitioned between 50 ml of an ice-water mixture and 75 ml of ether. The ether layer was separated, and the aqueous layer extracted with three 75 ml portions of ether. The ether extracts were combined and dried, and the ether removed therefrom by evaporation in vacuo. The resulting residue consisted of 4-[(1-acetyl-4-piperidyl)-1,2-epoxy-1-propyl]quinoline.

Hydrolysis of the acetyl group of the above compound with dilute base yielded a mixture of racemic erythro and racemic threo rubanol, which was separated into its components by procedures of the prior art.

EXAMPLE 7

Preparation of Cinchonidine and Cinchonine

Following the procedure of Example 6, methylene diphenylsulfurane was prepared from diphenylmethylsulfonium tetrafluoroborate, lithium di-isopropylamide and n-butyl-lithium. Reaction of the sulfurane with 4-methylsulfonylquinoline yielded the corresponding sulfur ylid. Still following the procedure of Example 6, reaction of the ylid at −50° C. with N-acetyl-3(R)-vinyl-4(S)-piperidineacetaldehyde yielded racemic 4-[3-(3(R)-vinyl-1-acetyl-4(S)-piperidyl)-1,2-epoxy-1-propyl]quinoline.

Treatment of the above epoxide with alkali as in the previous example yielded a mixture of cinchonine, cinchonidine, epicinchonine and epicinchonidine. Preparative thin layer chromatography on silica gel plates yielded cinchonidine, cinchonine, and a mixture of the epi-cinchonine and epi-cinchonidine.

I claim:

1. A process for preparing a compound of the formula

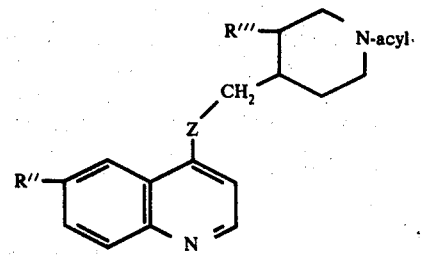

wherein R″ is H or methoxy, R‴ is H or vinyl and Z is vinyl which comprises the steps of reacting a quinoline of the formula:

3,989,691

13

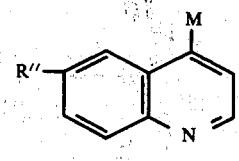

wherein R'' is H or methoxy and M is a group labile to nucleophilic displacement of the class consisting of halo, $C_1$-$C_4$ alkylsulfonyl, $C_1$-$C_4$ alkyl sulfonyloxy, $C_1$-$C_4$ alkylmercapto, aryl sulfonyl, aryl mercapto and aryl sulfonyloxy wherein aryl is phenyl, α or β naphthyl, or substituted phenyl wherein said substituents are members of the group trifluoromethyl, halo, methyl, methoxy, ethyl, ethoxy, acetyl, or propionyl;

with a phosphorane [$CH_2$=P(R'''')$_3$] wherein each R'''' independently represents phenyl or $C_1$-$C_4$ alkyl, or one equivalent of said phosphorane and one equivalent of a strong, non-nucleophilic base of the group sodium or potassium hydride, butyl lithium, diazabicyclononane, diazabicycloundecane, potassium t-butoxide, lithium di-isopropyl amide, sodium methylate or sodium amide;

to form an ylid of the formula

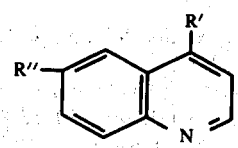

wherein R'' is H or methoxy and R' is CH=P(R'''')$_3$ wherein each R'''' independently represents phenyl and $C_1$-$C_4$ alkyl and then reacting said ylid with an N-acyl-4-piperidylacetaldehyde of the formula:

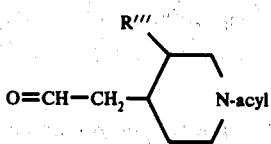

wherein R''' is H or vinyl and then isolating the product of said ylid reaction.

2. The process which comprises the steps of
1. reacting a substituted quinoline of the formula:

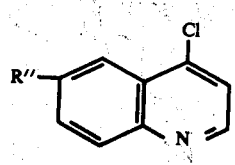

wherein R'' is H or OCH$_3$;
with two equivalents of methylene triphenylphosphorane or with one equivalent of methylene triphenylphosphorane and one equivalent of NaH to yield an ylid of the formula:

14

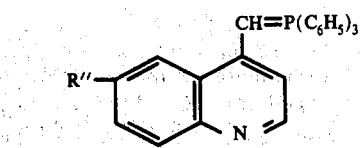

wherein R'' is H or OCH$_3$;
and then
2. reacting said ylid with a substituted piperidine of the formula:

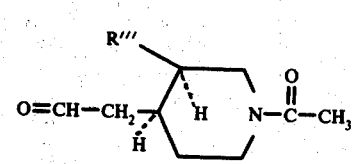

wherein R''' is H or vinyl; to yield a compound of the formula:

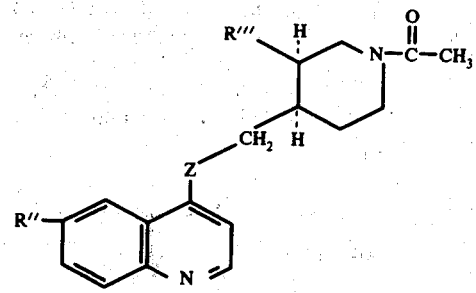

wherein Z is CH=CH and R'' and R''' have the same meaning as hereinabove.

3. A process for preparing a compound of the formula

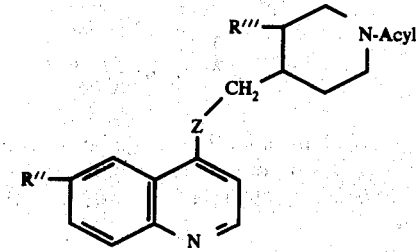

wherein R'' is H or methoxy, R''' is H or vinyl and Z is 1,2-epoxy which comprises the steps of reacting a quinoline of the formula

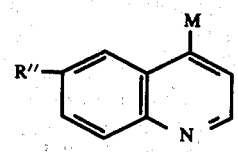

wherein R'' is H or methoxy and M is a group labile to nucleophilic displacement of the class consisting of halo, $C_1$–$C_4$ alkylsulfonyl, $C_1$–$C_4$ alkyl sulfonyloxy, $C_1$–$C_4$ alkylmercapto, aryl sulfonyl, aryl mercapto and aryl sulfonyloxy wherein aryl is phenyl, α or β-naphthyl or substituted phenyl wherein said substituents are members of the group trifluoromethyl, halo, methyl, methoxy, ethyl, ethoxy, acetyl, or propionyl with a sulfurane [$CH_2$=S(R'''')$_2$] wherein each R'''' independently represents phenyl or $C_1$–$C_4$ alkyl, or with one equivalent of said sulfurane and one equivalent of a strong, non-nucleophilic base of the group sodium or potassium hydride, butyl lithium, diazabicyclononane, diazabicyloundecane, potassium t-butoxide, lithium di-isopropyl amide, sodium methylate or sodium amide to form an ylid of the formula

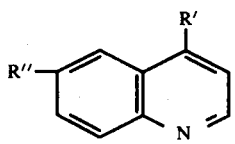

wherein R'' is H or methoxy and R' is CH=S(R'''')$_2$ wherein R'''' represents independently phenyl and $C_1$–$C_4$ alkyl
and then reacting said ylid with an N-acyl-4-piperidylacetaldehyde of the formula

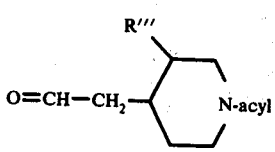

wherein R''' is H or vinyl and then isolating the product of said ylid reaction.

4. The process which comprises the steps of
1. reacting a substituted quinoline of the formula:

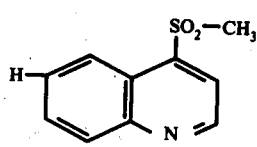

with two equivalents of methylene diphenylsulfurane or with one equivalent of methylene diphenylsulfurane and one equivalent of NaH, to yield an ylid of the formula:

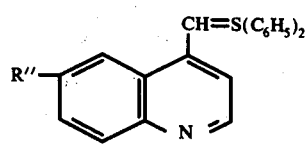

wherein R'' is H or OCH$_3$; and then
2. reacting said ylid with a substituted piperidine of the formula:

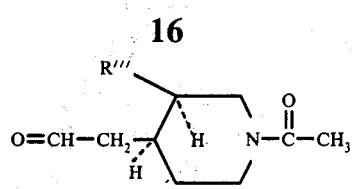

wherein R''' is H or vinyl; to yield a a compound of the formula:

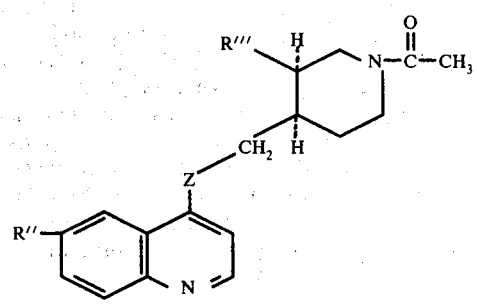

wherein Z is 1,2-epoxy and R'' and R''' have the same meaning as hereinabove.

5. A process according to claim 1 in which 4-chloro-6-methoxy quinoline is reacted with two equivalents of methylene triphenylphosphorane or with one equivalent of methylene triphenylphosphorane and one equivalent of NaH to yield a phosphorus ylid of the formula:

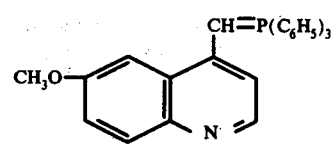

and then said phosphorus ylid is reacted with N-acetyl-3(R)-vinyl-4(S)-piperidineacetaldehyde to yield a compound of the formula:

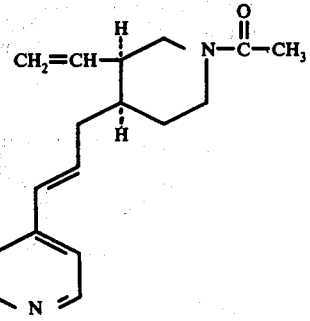

6. A process for preparing a compound of the formula

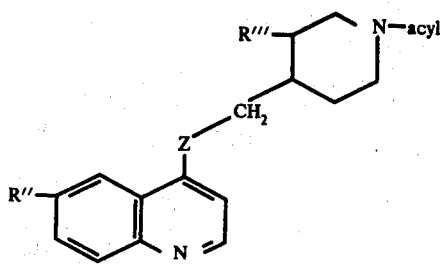

wherein R'' is H or methoxy, R''' is H or vinyl and Z is vinyl which comprises the steps of reacting a quinoline of the formula

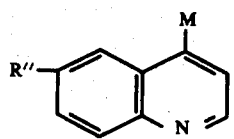

wherein R'' is H or methoxy and M is chloro, bromo, $C_1$–$C_4$ alkyl or aryl mercapto or $C_1$–$C_4$ alkyl or aryl sulfonyl with two equivalents of a phosphorane [$CH_2$=P(R'''')$_3$] or one equivalent of said phosphorane and one equivalent of a strong base of the group consisting of sodium hydride, potassium hydride, lithium di-isopropylamide, diazabicyclononane, diazabicycloundecane, butyl lithium, potassium t-butoxide, sodium methylate and sodium amide, wherein each R'''' independently represents phenyl or $C_1$–$C_4$ alkyl, to form an ylid of the formula

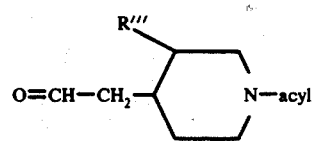

wherein R'' is H or methoxy; and then reacting said ylid with an N-acyl-4-piperidylacetaldehyde of the formula

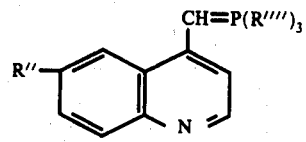

wherein R''' is H or vinyl and then isolating the product of said ylid reaction.

7. A process according to claim 1 in which M is halo, $C_1$–$C_4$ alkylsulfonyl, $C_1$–$C_4$ alkylmercapto, arylsulfonyl or arylmercapto wherein aryl is phenyl, tolyl, trifluoromethylphenyl, halophenyl, anisyl, phenetolyl, ethylphenyl, nitrophenyl, acetylphenyl or propionylphenyl.

8. A process according to claim 3 in which M is halo, $C_1$–$C_4$ alkylsulfonyl, $C_1$–$C_4$ alkylmercapto, arylsulfonyl or arylmercapto wherein aryl is phenyl, tolyl, trifluoromethylphenyl, halophenyl, anisyl, phenetolyl, ethylphenyl, nitrophenyl, acetylphenyl or propionylphenyl.

* * * * *